United States Patent

Wolter et al.

[11] Patent Number: 5,399,738
[45] Date of Patent: Mar. 21, 1995

[54] SILANES, PROCESS FOR THEIR PREPARATION AND THEIR APPLICATION TO PREPARE POLYMERS AND POLYCONDENSATES

[75] Inventors: Herbert Wolter, Gerchsheim; Klaus Rose, Kitzingen; Christian Egger, Höchberg, all of Germany

[73] Assignee: Fraunhofer-Gesellschaft zur Forderung der Angewandten Forschung E.V., Munich, Germany

[21] Appl. No.: 680,928

[22] Filed: Apr. 5, 1991

[30] Foreign Application Priority Data

Apr. 5, 1990 [DE] Germany .................. 40 11 044.3

[51] Int. Cl.$^6$ .................. C07F 7/08; C07F 7/10; C07F 7/18
[52] U.S. Cl. .................. 556/420; 556/404; 556/405; 556/410; 556/411; 556/421; 556/436; 556/437; 556/442
[58] Field of Search .................. 556/427, 410, 411, 436, 556/420, 421, 442, 437, 404, 405

[56] References Cited

U.S. PATENT DOCUMENTS

| | | |
|---|---|---|
| 4,491,650 | 1/1985 | Rizk et al. . |
| 4,625,007 | 11/1986 | Ellis et al. . |
| 4,754,012 | 6/1988 | Yoldas et al. . |
| 4,997,965 | 3/1991 | Lohmann et al. .............. 556/427 X |
| 5,079,312 | 1/1992 | Isozaki et al. . |

*Primary Examiner*—Paul F. Shaver

*Attorney, Agent, or Firm*—Oblon, Spivak, McClelland, Maier & Neustadt

[57] ABSTRACT

Silanes of the general formula (I):

$$\{(X_aR_bSi(R'(A)_c)_{(4-a-b)}\}_xB \quad (I)$$

in which the groups and indices have the following meaning:
X: hydrogen, halogen, hydroxy, alkoxy, acyloxy, alkyl carbonyl, alkoxycarbonyl or —NR''$_2$;
R: alkyl, alkenyl, aryl, alkaryl, or aralkyl;
R': alkylene, arylene or alkylene arylene;
R'': hydrogen, alkyl or aryl;
A: O, S, PR'', POR'', NHC(O)O or NHC(O)NR'';
B: straight chain or branched organic group, which is derived from a B' compound with at least one C=C double bond for c=1 and A=NHC(O)O or NHC(O)NR'') or at least two C=C double bonds, and 5 to 50 carbon atoms;
a: 1, 2 or 3;
b: 0, 1 or 2;
c: 0 or 1;
x: whole number, whose maximum value corresponds to the number of double bonds in compound B' minus 1, or is equal to the number of double bonds in compound B', when c=1 and A stands for NHC(O)O or NHC(O)NR'';

are suitable to prepare homo and copolycondensates and homo or copolymers according to the sol-gel method or by photochemical or thermal polymerization.

18 Claims, No Drawings

SILANES, PROCESS FOR THEIR PREPARATION AND THEIR APPLICATION TO PREPARE POLYMERS AND POLYCONDENSATES

BACKGROUND OF THE INVENTION

1. Field of the Invention

The present invention is directed to novel silane compounds, and more specifically, to modified silanes containing reactive C=C double bonds.

2.. Discussion of the Background commercial silanes with reactive double bonds represent in general monofunctional compounds with a C=C double bond, e.g., (meth)acryloxysilanes of the following type:

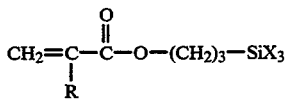

where R denotes hydrogen or methyl and X is, e.g., halogen or alkoxy.

Silanes of this type have, as a rule, low molecular weights and thus, prior to the Si—X hydrolysis and condensation, are relatively volatile compounds, which may have toxicological problems due to the presence of the acrylic groups. During further processing by polymerization or modifying functionalization, these silanes also have the drawback that due to the presence of only one reactive C=C double bond, only chain polymers can be obtained. Additionaly, during functionalization this C=C double bond, which is mandatory for the polymerization, is usually lost. Furthermore, as a rule, there is only a short carbon chain between the double bond and the silicon atom that is capable of forming an inorganic network so that the mechanical properties (flexibility, etc.) can be varied only to a limited degree.

SUMMARY OF THE INVENTION

Therefore, One object of the invention is to provide new, modified silanes in which the distance between a silicon atom and the reactive double bond can be set arbitrarily.

Another object is to provide organic silanes which can contain several reactive double bonds with the possibility of three dimensional crosslinking and which can contain other functional groups, which allow a targeted adaptation to the desired field of application.

These and other objects have been achieved by the present silanes which have general formula (I):

in which the groups have the following meanings:

X: hydrogen, halogen, hydroxy, alkoxy, acyloxy, alkyl carbonyl, alkoxycarbonyl or —NR''$_2$;
R: alkyl, alkenyl, aryl, alkaryl, or aralkyl;
R': alkylene, arylene or alkylene-arylene;
R'': hydrogen, alkyl or aryl;
A: O, S, PR'', POR'', NHC(O)O or NHC(O)NR'';
B: straight chain or branched organic group, which is derived from a compound B' which has at least one C=C double bond for c=1 and A=NHC(O)O or NHC(O)NR'', or at least two C=C double bonds, and 5 to 50 carbon atoms;
a: 1, 2 or 3;
b: 0, 1 or 2;
c: 0 or 1;
X: whole number, whose maximum value corresponds to the number of double bonds in compound B' minus 1, or is equal to the number of double bonds in compound B' when c=1 and A stands for NHC(O)O or NHC(O)NR''.

DETAILED DESCRIPTION OF THE PREFERRED EMBODIMENTS

In the present invention, the alkyl groups are, e.g., straight chain, branched or cyclic groups having 1 to 20, preferably 1 to 10 carbon atoms and preferably lower alkyl groups having 1 to 6, preferably 1 to 4 carbons atoms. Specific examples are methyl, ethyl, n-propyl, isopropyl, n-butyl, sec-butyl, tert-butyl, isobutyl, n-pentyl, n-hexyl, cyclohexyl, 2-ethylhexyl, dodecyl and octadecyl.

The alkenyl groups are, e.g., straight chain, branched or cyclic groups having 2 to 20, preferably 2 to 10 carbon atoms and preferably lower alkenyl groups having 2 to 6 carbon atoms, such as vinyl, allyl, and 2-butenyl.

Preferred aryl groups are phenyl, bisphenyl and naphthyl. The alkoxy, acyloxy, alkylamino, dialkylamino, alkylcarbonyl, alkoxycarbonyl, aralkyl, alkaryl, alkylene, arylene and alkylene-arylene groups are derived preferably from the aforementioned alkyl and aryl groups. Specific examples are methoxy, ethoxy, n- and i-propoxy, n-, i-, sec- and tert-butoxy, monomethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenyl-ethyl and tolyl.

The groups cited may optionally carry one or more substituents, e.g., halogen, alkyl, hydroxyalkyl, alkoxy, aryl, aryloxy, alkylcarbonyl, alkoxycarbonyl, furfuryl, tetrahydrofurfuryl, amino, monoalkylamino, dialkylamino, trialkylammonium, amido, hydroxy, formyl, carboxy, mercapto, cyano, nitro, epoxy, SO$_3$H or PO$_4$H$_2$.

Among the halogens, preferred are fluorine, chlorine and bromine and in particular chlorine.

For a≧2 or b=2, the X and R groups may have the same or a different meaning.

In the preferred silanes of the aforementioned formulas X, R, R', A, a, b, c and x are defined as follows
X: (C$_1$-C$_4$)-alkoxy, in particular methoxy and ethoxy; or halogen, in particular chlorine;
R: (C$_1$-C$_4$)-alkyl, in particular methyl and ethyl;
R': (C$_1$-C$_4$)-alkylene, in particular methylene and propylene;
A: O or S, in particular S;
a: 1, 2 or 3;
(4-a-b): 0 for c=0 and 1 for c=1;
c: 0 or 1, preferably 1;
x: 1 or 2.

It is especially preferred if the structural unit with the index x is selected from triethoxysilyl, methyl-diethoxysilyl, methyl-dichlorosilyl, 3-methyl-dimethoxysilyl-propylthio, 3-trimethoxysilyl-propylthio, methyl-diethoxysilyl-methylthio and ethoxy-dimethylsilyl-methylthio.

The B group is derived from a substituted or unsubstituted compound B' with at least one or at least two C=C double bonds, e.g., vinyl, allyl, acrylic and/or methacrylic groups, and 5 to 50, preferably 6 to 30 carbon atoms. Preferably B is derived from a substituted or unsubstituted compound B' with two or more acrylate and/or methacrylate groups (such compounds are called (meth)acrylates below.

If compound B' is substituted, the substituents can be selected from among the aforementioned substituents.

To prepare the mono(meth)acryloxysilanes of the invention, compound B' with two C=C double bonds is added; to prepare poly(meth)acryloxysilanes, those with at least three C=C double bonds are added. Specific examples for such compounds are the following (meth)acrylates:

$$CH_2=C(CH_3)-C(O)-O-C(CH_3)=CH_2$$

$$CH_2=C(CH_3)-C(O)-O-CH_2-CH=CH_2$$

$$CH_2=C(CH_3)-C(O)-O-CH_2-CH_2-O-C(O)-C(CH_3)=CH_2$$

$$CH_2=C(CH_3)-C(O)(-O-CH_2-CH_2)_2-O-C(O)-C(CH_3)=CH_2$$

$$CH_2=C(CH_3)-C(O)(-O-CH_2-CH_2)_3-O-C(O)-C(CH_3)=CH_2$$

$$CH_2=C(CH_3)-C(O)(-O-CH_2-CH_2)_4-O-C(O)-C(CH_3)=CH_2$$

$$CH_2=C(CH_3)-C(O)(-O-CH_2-CH_2)_n-O-C(O)-C(CH_3)=CH_2, \quad n=9$$

$$CH_2=C(CH_3)-C(O)-O-CH(CH_3)-CH_2-CH_2-O-C(O)-C(CH_3)=CH_2$$

$$CH_2=C(CH_3)-C(O)-O-(CH_2)_4-O-C(O)-C(CH_3)=CH_2$$

$$CH_2=C(CH_3)-C(O)-O-(CH_2)_6-O-C(O)-C(CH_3)=CH_2$$

$$CH_2=C(CH_3)-C(O)-O-(CH_2)_{12}-O-C(O)-C(CH_3)=CH_2$$

$$CH_2=C(CH_3)-C(O)-O-CH_2-C(CH_3)_2-CH_2-O-C(O)-C(CH_3)=CH_2$$

$$[CH_2=C(CH_3)-C(O)-O-CH_2-CH_2-O-C(O)-NH-]_2 C_9H_{10}$$

$$CH_2=C(CH_3)-C(O)-CH_2-C(CH_2-CH_3)(CH_2-O-C(O)-C(CH_3)=CH_2)_2$$ with the third branch being $CH_2-O-C(O)-C(CH_3)=CH_2$ $$CH_2=CH-C(O)-NH-CH_2-NH-C(O)-CH=CH_2$$

$$CH_2=CH-C(O)-O-C(O)-CH=CH_2$$

$$CH_2=CH-C(O)-O-CH_2-CH=CH_2$$

$$CH_2=CH-C(O)-O-CH_2-CH_2-O-C(O)-CH=CH_2$$

$$CH_2=CH-C(O)(-O-CH_2-CH_2)_2-O-C(O)-CH=CH_2$$

$$CH_2=CH-C(O)(-O-CH_2-CH_2)_3-O-C(O)-CH=CH_2$$

$$CH_2=CH-C(O)(-O-CH_2-CH_2)_4-O-C(O)-CH=CH_2$$

$$CH_2=CH-C(O)(-O-CH_2-CH_2)_n-O-C(O)-CH=CH_2, \quad n=9$$

$$CH_2=CH-C(O)-O-CH(CH_3)-CH_2-CH_2-O-C(O)-CH=CH_2$$

$$CH_2=CH-C(O)-O-(CH_2)_4-O-C(O)-CH=CH_2$$

$$CH_2=CH-C(O)-O-(CH_2)_6-O-C(O)-CH=CH_2$$

$$CH_2=C(CH_3)-C(O)-NH-CH_2-NH-C(O)-C(CH_3)=CH_2$$

$$CH_2=CH-C(O)-O-(CH_2)_{12}-O-C(O)-CH=CH_2$$

$$CH_2=CH-C(O)-O-CH_2-C(CH_3)_2-CH_2-O-C(O)-CH=CH_2$$

-continued
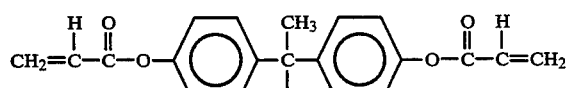
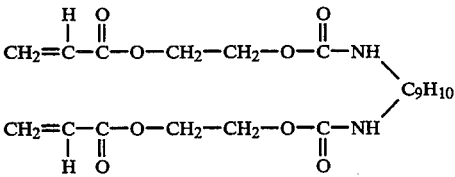
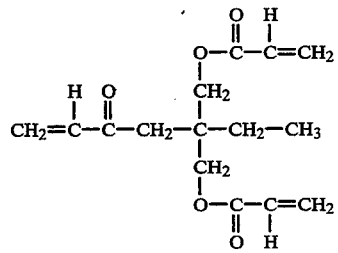
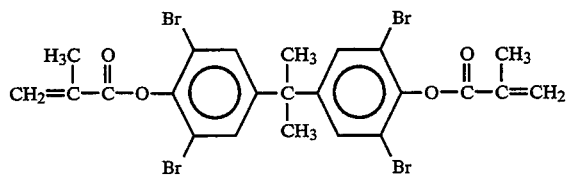
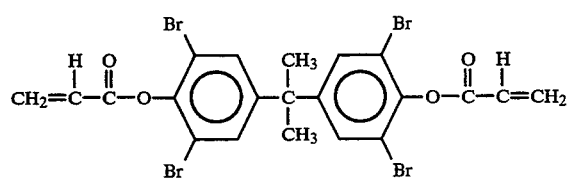
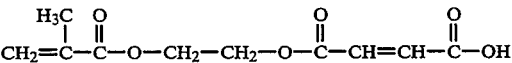
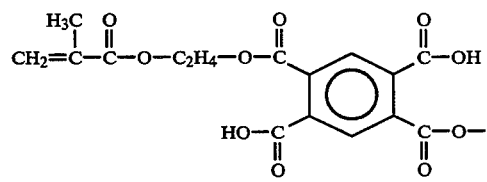
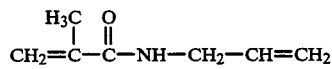
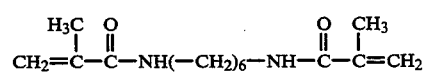
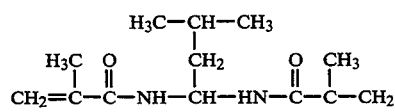
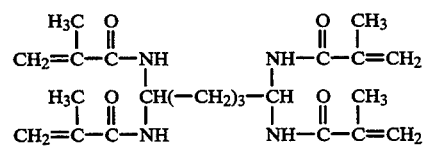
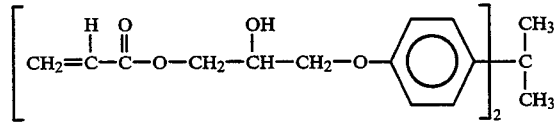
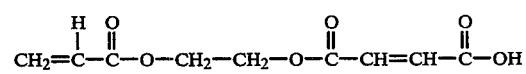
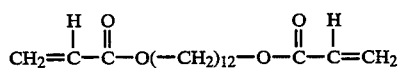
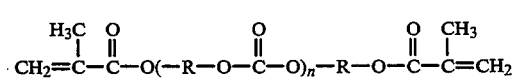
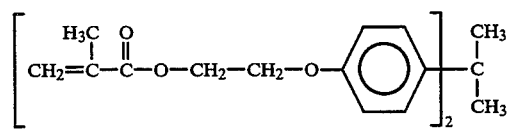
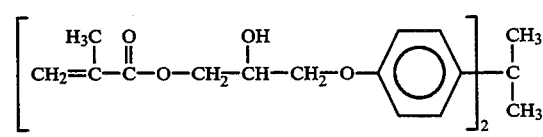
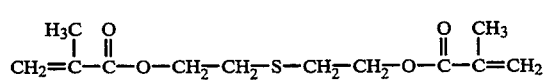
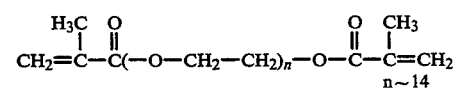
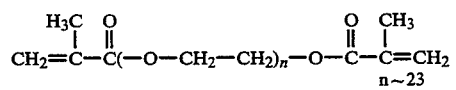
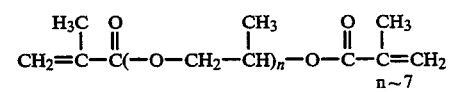
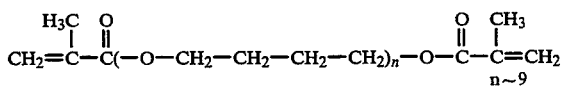

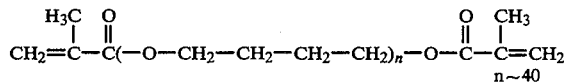

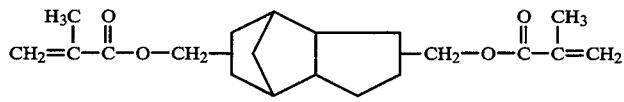

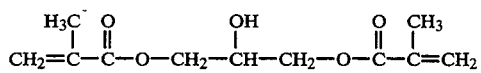

Preferred acrylates are, e.g., the acrylates of trimethylol propane, pentaerythritol, and dipentaerythritol. Examples include trimethylol propane triacrylate (TMPTA), pentaerythritol triacrylate (PETA), pentaerythritol tetracrylate and dipentaerythritol pentaacrylate.

Other examples for preferred (meth)acrylates are those of the formula

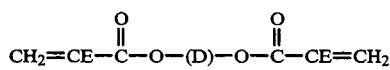

where E stands for H or $CH_3$ and D is an organic group, as contained, e.g., in the aforementioned specific compounds and/or in the compounds described in the following examples.

Thus, D can be derived, e.g., from $C_2$–$C_6$-alkanediols (e.g., ethylene glycol, propylene glycol, butylene glycol, 1,6-hexanediol), polyethylene glycols or polypropylene glycols (e.g., those of formula HO—($CH_2$—CHR'''—O$)_n$H, where R''' is H or $CH_3$ and n=2-10) or can be derived from optionally substituted and/or alkoxylated (e.g., ethoxylated and/or propoxylated) bisphenol A.

The silanes of the present invention can be prepared, e.g., as follows a) a silane of the general formula (II):

$$X_aR_bSiR'Y \qquad (II)$$

in which X, R, R', a and b have the aforementioned meanings, (a+b)=3 and Y denotes the group SH, PR''H or POR''H, is subjected to an addition reaction with a compound B' having at least two C=C double bonds; or b) a silane of the general formula (III):

$$X_aR_bSiR'NCO \qquad (III)$$

in which X, R, R' a and b have the aforementioned meanings and (a+b)=3, is subjected to a condensation reaction with a hydroxyl or amino-substituted compound B' having at least one C=C double bond; or c) a silane of the general formula (IV):

$$X_aR_bSiH \qquad (IV)$$

in which X, R, R', a and b have the aforementioned meanings and (a+b)=3, is subjected to a hydrosilylation reaction with a compound B' having at least two C=C double bonds.

The silanes of the general formulas (II) to (IV) are either commercially available or can be prepared according to known methods. W. Noll, "Chemie und Technologie der Silicone", Verlag Chemie GmbH, Weinheim/Bergstraße (1968).

In process embodiment (a), the silanization takes place by means of one of the C=C double bonds of the B' compounds, where, e.g., the mercapto group of a corresponding silane is added through a base catalyzed Michael reaction, forming a thioether unit. The phosphine is added in an analgous manner.

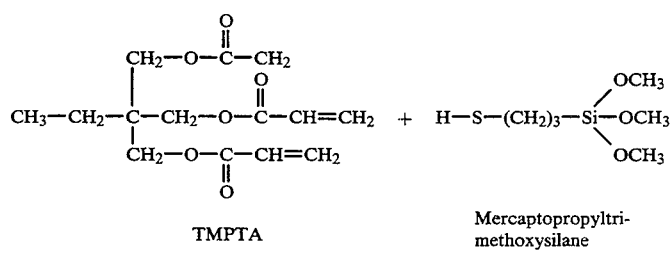

TMPTA    Mercaptopropyltrimethoxysilane

↓ KOH

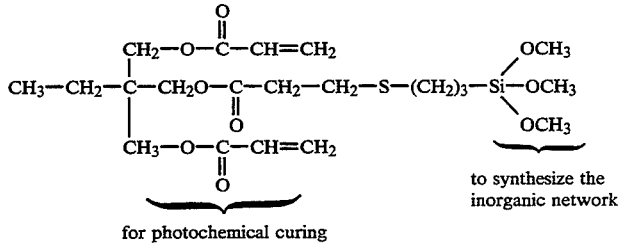

for photochemical curing / to synthesize the inorganic network

FIG. 1. Reaction involving thiol addition

In process embodiment (b), a urethane (or urea) structure is produced through silanization of the hydroxyl or amino substituted starting compound B' with an isocyanatosilane.

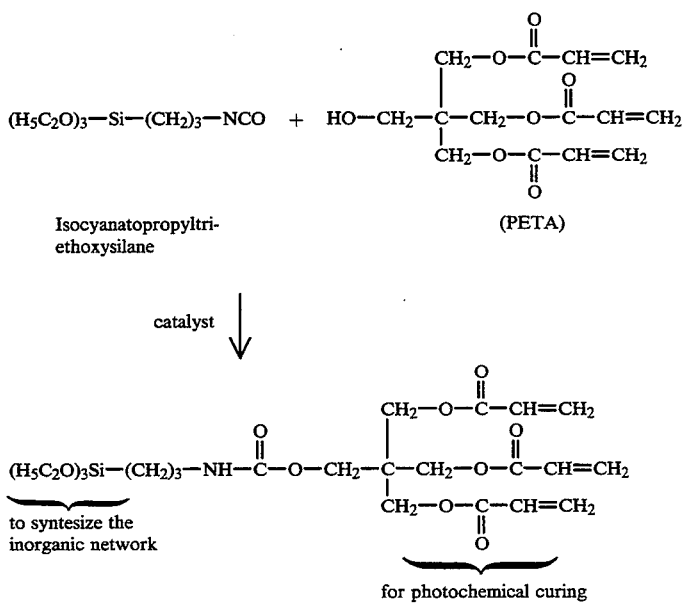

FIG. 2. Reaction involving formation of a urethane

In process embodiment (c), the hydrosilylation takes place schematically according to the following reaction equation:

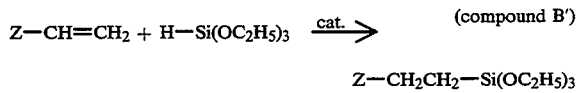

FIG. 3. Reaction involving of hydrosilylation

The hydrolyzable groups contained in the resulting silane (e.g., alkoxy groups) guarantee that an inorganic network can be synthesized with Si—O—Si units, whereas the double bond(s) contained in the B group can be polymerized while synthesizing an organic network.

To synthesize the inorganic network the silanes of the invention are hydrolyzed and polycondensed with or without the addition of other cocondensable components. Preferably the polycondensation is conducted according to the sol-gel method, as described in DE-A1 27 58 414, 27 58 415, 30 11 761, 38 26 715 and 38 35 968.

To synthesize the organic network, the silanes of the invention are polymerized with or without the addition of other copolymerizable components (e.g., the silane-free B' compounds). The polymerization can be conducted, e.g., thermally or photochemically using methods that are described in DE-A1 31 43 820, 38 26 715 and 38 35 968. See also U.S. Pat. No. 5,233,006 incorporated herein by reference.

The course of the inorganic crosslinking can be examined, e.g., by means of Karl Fischer titration (determination of water consumption during hydrolysis); the course of photochemical curing by means of IR spectroscopy (intensity and relation of the C=C and C=O bands).

The silanes of the invention represent highly reactive systems, which cure into mechanically stable coatings or molded parts, e.g., with ultraviolet irradiation within a short time, even as short as fractions of a second.

They can be prepared by means of simple addition reactions, and by suitably selecting the starting compounds they can exhibit a variable number of reactive groups with the most variable functionality. When two or more C=C double bonds are present, the formation of a three dimensional organic network is possible. Furthermore, the introduction of other functional groups at existing C=C double bond sites is possible, where the remaining double bonds are available for organic polymerization.

The mechanical (e.g., flexibility) and physical-chemical properties (adsorption, color, absorption characteristics, refractive index, adhesion etc.) of the products can be affected by means of the distance between the silicon atoms and the functional organic groups, i.e., by means of the chain length, and by means of the presence of other functional groups in this chain.

Depending on the type and number of the hydrolyzable groups (e.g., alkoxy groups), silicone or glass-like properties can be obtained with the design of the inorganic network.

The silanes of the invention have a relatively high molecular weight and correspondingly reduced volatibility as compared to the conventional pure acrylate monomers so that the toxicity risk during processing and application is lower. Inorganic and/or organic crosslinking produce polysiloxanes with still lower volatibility, thus eliminating the toxicity problem of the acrylate components.

The silanes of the present invention can be used either as such or, preferably following prior hydrolytic (pre)-condensation, in compositions, which also contain additives adapted to the purpose of the application, e.g., usual paint additives, solvents, fillers, photoinitiators, thermal initiators, flow control agents and pigments.

The silanes or the silane-containing compositions (including the corresponding polycondensates) are suitable, e.g., for use as or in coating, filler or bulk materials, adhesive(s), coupling agent(s) and injection molding compounds. Due to their relatively high molecular weight, they experience only negligble shrinkage when curing. Coatings and molded parts made of the silanes of the invention have the advantage that they can be photochemically structured. Specific fields of application are, e.g., the coating of substrates made of glass, wood, metal, plastic, paper, ceramic, etc. by dipping, pouring, spreading, spraying, rolling, centrifuging, electrostatic spraying, electronic dipping, etc., and useful for optical, optoelectronic or electronic components.

Other features of the invention will become apparent in the course of the following descriptions of exemplary embodiments which are given for illustration of the invention and are not intended to be limiting thereof.

EXAMPLES

The following starting materials are used in these examples;

| | |
|---|---|
| silane I: | HS—(CH$_2$)$_3$—SiCH$_3$(OCH$_3$)$_2$ |
| silane II: | HS—CH$_2$—SiCH$_3$(OC$_2$H$_5$)$_2$ |
| silane III: | HS—(CH$_2$)$_3$—Si(OCH$_3$)$_3$ |
| silane IV: | HSiCH$_3$(OC$_2$H$_5$)$_2$ |
| silane V: | HSi(OC$_2$H$_5$)$_3$ |
| silane VI: | HSiCH$_3$Cl$_2$ |
| silane VII: | HS—CH$_2$—Si(CH$_3$)$_2$OC$_2$H$_5$ |
| silane VIII: | OCN—(CH$_2$)$_3$—Si(OC$_2$H$_5$)$_3$ |
| acrylate A: | 1,6-hexanediol diacrylate |
| acrylate B: | tripropylene glycol diacrylate |
| acrylate C: | 2,2-di[4-(2-hydroxyethoxy)phenyl]propane diacrylate |
| acrylate D: | di(trimethylol propane)tetraacrylate |
| acrylate E: | 1,2,3-tri(3-hydroxypropoxy)propane triacrylate |
| acrylate F: | tris(2-hydroxyethyl)isocyanurate triacrylate |
| acrylate G: | 2,2-di[4-(2-hydroxyethoxy)phenyl]propane dimethacrylate |
| acrylate H: | 2,2-di[3,5-dibromo-4-(2-hydroxyethoxy)phenyl]propane dimethacrylate |
| acrylate I: | pentaerythritol tetraacrylate |
| acrylate J: | trimethylol propane triacrylate |
| acrylate K: | pentaerythritol triacrylate |
| acrylate L: | dipentaerythritol pentaacrylate |
| acrylate M: | bisphenol-A-dimethacrylate |
| acrylate N: | trimethylol propane trimethacrylate |
| acrylate O: | glycerol-1,3-dimethacrylate |

EXAMPLE 1

Preparation of the compound of the formula

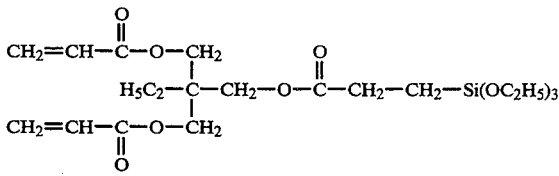

Compound (1)

0.1 mole (29.5 g, 26.6 ml) acrylate J were reacted with 0.1 mole (16.5 g, 18.8 ml) silane V in 100 ml solvent (e.g., ethanol, benzene, cyclohexane, diethyl ether or methyl-tert.-butyl ether). To this solution were added 0.3 mmol (930 mg) of the catalyst ([Rh(CO)Cl(PPh$_2$CH$_2$CH$_2$SiO$_{1.5}$].40 SiO$_2$ (BET surface area=723.5 m$^2$ average pore radius 1.94 nm, average pore volume 0.70 cm$^3$/g) and stirred in the dark at 40±3° C. until in the IR spectrum no more Si—H vibrations could be detected (48 to 72 hours). Following completion of the reaction, the catalyst was filtered off and the solvent was removed under vacuum.

Yield 43.5 g (94%) of the yellowish, light-sensitive oil, boiling point 202° C. (decomposition).

| C$_{21}$H$_{36}$O$_9$Si | molecular weight: 460.60 | |
|---|---|---|
| calculated: | C 54.76% | H 7.88% |
| found: | C 56.02% | H 7.69% |

$^1$H—NMR (CDCl$_3$): δ = 5.6–7.1 (m; —C$\underline{H}$=C$\underline{H}_2$; 6H)

3.2–4.2 (m; —OC$\underline{H}_2$—; 12H)

2.0–2.5 (t; —C$\underline{H}_2$COO—; 2H)

0.3–1.8 (m; —C$\underline{H}_3$, —C$\underline{H}_2$—; 16H)

$^{29}$Si—NMR (CDCl$_3$): δ = −24.1 (s)

EXAMPLE 2

Preparation of the compound of the formula

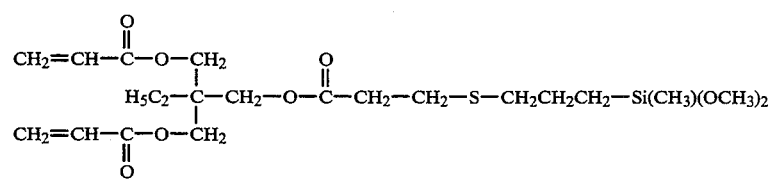

Compound (2) 0.15 mole (44.45 g) acrylate J were introduced under nitrogen atmosphere while cooling in a water bath to 20° C. and quickly reacted with 0.15 mole (27.05 g) silane I and 0.0015 mole (0.0842 g) KOH in 6 g of ethanol. The reaction mixture was stirred for 5 minutes (iodine-mercaptan test), then taken up in 200 ml of diethyl ether, shaken and washed frequently with 20 ml of H₂O until the wash water reacted neutrally. The Compound (5)

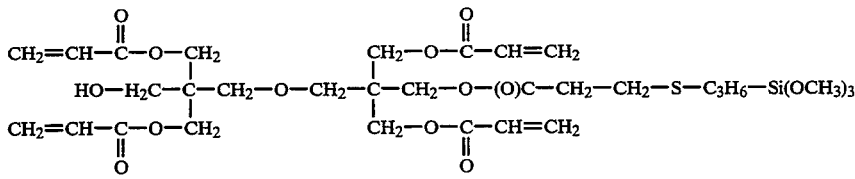

ether phase was dried, e.g., over Na₂SO₄ or with a hydrophobic filter and concentrated by evaporation at 35°–40° C. using aspirator vacuum. Finally the residue was dried for about 1 hour under a high vacuum at 35°–40° C.

EXAMPLE 3

Preparation of the compound of the formula (compound 3)

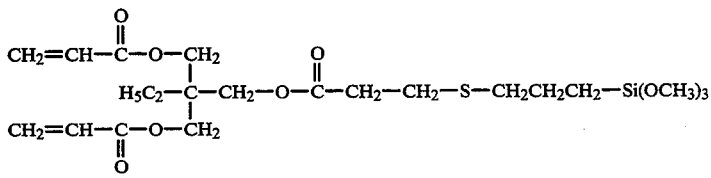

The preparation was conducted as in example 2 using an equimolar quantity of silane III instead of silane I.

EXAMPLE 4

Preparation of the compound of the formula (compound 4)

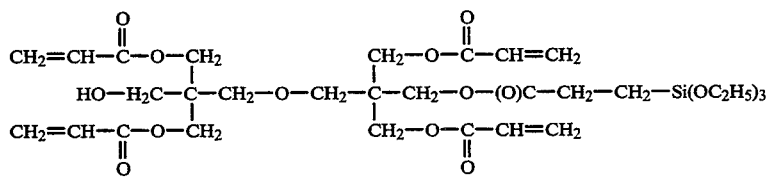

The preparation was conducted as in example 1 using an equimolar quantity of acrylate L instead of acrylate J. A yellowish, light sensitive oil was obtained.

| C₃₁H₄₇O₁₅Si | molecular weight: 687.80 | |
|---|---|---|
| calculated: | C 54.14% | H 6.89% |
| found: | C 54.47% | H 7.11% |

¹H—NMR (CDCl₃): δ = 5.8–6.9 (m; —C$\underline{H}$=C$\underline{H}_2$; 12H)

3.3–4.7 (m; —OC$\underline{H}_2$—; 22H)

2.2–2.8 (m; —C$\underline{H}_2$COO, —O$\underline{H}$; 3H)

1.2 (t; —OCH₂C$\underline{H}_3$—; 9H)

1.0 (t; —SiC$\underline{H}_2$—; 2H)

²⁹Si—NMR (CDCl₃): δ = −26.3 (s)

EXAMPLE 5

Preparation of the compound of the formula

The preparation was conducted as in example 3 using an equimolar quantity of acrylate L instead of acrylate J.

EXAMPLE 6

Alternative preparation of the compound 2 of example 2

18 g (0.1 mole) silane I were added to 29.6 g (0.1 mole) acrylate J, dissolved in 50 ml of ethyl acetate, at 5° C. (ice cooling) under a nitrogen atmosphere. Again at 5° C. and under nitrogen atmosphere the resulting mixture was slowly reacted (drop-by-drop) with 0.0561 g (0.001 mole) KOH, dissolved in 5 g of ethanol. In so doing, the feed velocity was set in such a manner that the temperature of the reaction mixture remained clearly under 40° C. After a few minutes of stirring at 5° C., the reaction was checked (with the absence of free mercaptosilane the iodine, the mercaptan test was negative). Following completion of the reaction, the reaction mixture was reacted with 50 ml of ethyl acetate and washed with 30 ml portions of water until the eluate reacted neutrally. The organic phase was then dried over Na₂SO₄ or filtered over a hydrophobic filter, subsequently concentrated by evaporation at 30° C. using a rotation evaporator and subsequently dried at 20°–30° under high vacuum. Yield 44 g=93% (solid content 99%).

According to the process described in the above examples, the following silanes of the invention (1:1 adducts) were obtained. The silanes are characterized by a Roman number (starting silane) and a letter (starting acrylate).

| | |
|---|---|
| II-A | (compound 6) |
| I-A | (compound 7) |
| II-B | (compound 8) |
| I-B | (compound 9) |
| II-C | (compound 10) |
| I-C | (compound 11) |
| II-J | (compound 12) |
| I-E | (compound 13) |
| II-E | (compound 14) |
| I-F | (compound 15) |
| II-F | (compound 16) |
| IV-A | (compound 17) |
| V-A | (compound 18) |
| VI-J | (compound 19) |
| IV-J | (compound 20) |
| V-L | (2:1 adduct) (compound 21) |
| VII-J | (compound 22) |
| I-M | (compound 23) |
| I-H | (compound 24) |
| I-D | (compound 25) |
| III-K | (compound 26) |
| I-I | (compound 27) |
| I-L | (compound 28) |
| I-G | (compound 29) |
| I-N | (compound 30) |

Typical IR vibration bands of some of the above compounds are compiled in the following tables (absorbed as film between KBr sheets).

EXAMPLE 7

Preparation of the compound of the formula

Compound (31)

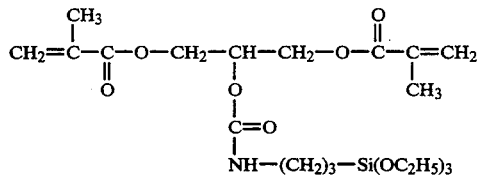

Under moisture-free atmosphere, 12.4 g (0.05 mole) silane VIII were slowly added drop-by-drop to 11.4 g (0.05 mole) acrylate O and 1.6 g (0.0025 mole) dibutyl tin didodecanoate (or an equivalent quantity of 1,4-diazabicyclo[2.2.2]octane). In so doing, the reaction mixture was observed. The reaction ended after about 1 hour (IR check, absence of free NCO groups). The desired compound was isolated in known manner. IR (film): 3380 (broad $v_{N-H}$), 1725 ($v_{C=O}$) and 1640 ($v_{C=C}$)cm$^{-1}$.

Obviously, numerous modifications and variations of the present invention are possible in light of the above teachings. It is therefore to be understood that within the scope of the appended claims, the invention may be practiced otherwise than as specifically described herein.

TABLE

Characteristic IR data and yield of the acrylate-silane of the invention.

| Compound number | $v(C=O)$ [cm$^{-1}$] | $v(C=C)$ [cm$^{-1}$] | Yield [%] |
|---|---|---|---|
| 2 | 1725–1745 | 1635, 1620 | 93 |
| 6 | 1720–1740 | 1635, 1620 | 82 |
| 7 | 1730–1740 | 1635, 1620 | 79 |
| 8 | 1730–1740 | 1640, 1620 | 87 |
| 9 | 1730–1740 | 1640, 1620 | 87 |
| 10 | 1730–1740 | 1635, 1610 | 82 |
| 11 | 1730–1745 | 1635, 1610 | 85 |
| 12 | 1730–1745 | 1635, 1620 | 91 |

TABLE-continued

Characteristic IR data and yield of the acrylate-silane of the invention.

| Compound number | $v(C=O)$ [cm$^{-1}$] | $v(C=C)$ [cm$^{-1}$] | Yield [%] |
|---|---|---|---|
| 13 | 1720–1740 | 1640, 1620 | 88 |
| 15 | 1710–1730 | 1635, 1620 | 89 |
| 16 | 1710–1730 | 1635, 1620 | 83 |
| 22 | 1730–1740 | 1630, 1615 | |
| 23 | 1740–1760 | 1640 | |
| 24 | 1730–1745 | 1640 | |
| 25 | 1730–1740 | 1640, 1620 | |
| 26 | 1730–1740 | 1640, 1620 | |
| 27 | 1730–1740 | 1640, 1620 | |
| 28 | 1730–1745 | 1640, 1620 | |
| 29 | 1730–1745 | 1640 | |

What is claimed as new and desired to be secured by Letters Patent of the United States is:

1. A silane of the formula (I):

$$(X_a R_b Si(R'(A)_c)_{(4-a-b)})_x B \tag{I}$$

wherein the groups and indices have the following meanings:
X: hydrogen, halogen, hydroxy, alkoxy, acyloxy, alkyl carbonyl, alkoxycarbonyl or —NR''$_2$;
R: alkyl, alkenyl, aryl, alkaryl, or aralkyl;
R': alkylene, arylene or alkylene arylene;
R'': hydrogen, alkyl or aryl;
A: O, S, PR'', POR'', NHC(O)O or NHC(O)NR'';
B: straight chain or branched organic group, which is derived from a B' compound with two or more acrylate groups, methacrylate groups or a combination thereof and 5 to 50 carbon atoms;
a: 1, 2 or 3;
b: 0, 1 or 2;
c: 0 or 1;
x: whole number, whose maximum value corresponds to the number of double bonds in compound B' minus 1, or is equal to the number of double bonds in compound B', when c=1 and A is NHC(O)O or NHC(O)NR''.

2. The silane of claim 1, wherein the groups and indices have the following meanings:
X: (C$_1$–C$_4$)-alkoxy or halogen;
R: (C$_1$–C$_4$) -alkyl;
R': (C$_1$–C$_4$)-alkylene;
A: O or S;
a: 1, 2 or 3;
(4-a-b): 0 for c=0 and 1 for c=1;
c: 0 or 1;
B and x: as defined in claim 1.

3. The silane of claim 1, wherein X is methoxy, ethoxy or chlorine.

4. The silane of claim 1, wherein R is methyl or ethyl.

5. The silane of claim 1, wherein R' is methylene or propylene.

6. The silane of claim 1, wherein A is S.

7. The silane of claim 1, wherein c=1.

8. The silane of claim 1, wherein the unit with the index x is selected from the group consisting of triethoxysilyl, methyl-diethoxysilyl, methyl-dichlorosilyl, 3-methyl-dimethoxysilylpropylthio, 3-trimethoxysilylpropylthio, ethoxy-dimethylsilylmethylthio, and methyl-diethoxysilylmethylthio.

9. The silane of claim 1, wherein compound B' contains at least three C=C double bonds.

10. The silane of claim 1, wherein B is derived from acrylates of trimethylol propane, pentaerythritol, dipentaerythritol, $C_2$-$C_6$-alkanediols, polyethylene glycols, polypropylene glycols, bisphenol A, substituted bisphenol A or alkoxylated bisphenol A.

11. The silane of claim 1, wherein x=1 or 2.

12. A process for preparing the silane of claim 1, comprising:

a) adding and reacting a silane of the formula (II):

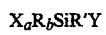   (II)

wherein X, R, R', a and b have the meanings given in claim 1, (a+b)=3 and Y is group SH, PR"H or POR"H with a compound B' having at least two acrylate groups, methacrylate groups, or a combination thereof; or b) condensing a silane of the formula (III):

   (III)

wherein X, R, R', a and b have the meanings given in claim 1, and (a+b)=3, with a hydroxyl or amino-substituted compound B' having at least two acrylate groups, methacrylate groups, or a combination thereof; or c) hydrosilylating a silane of the formula (IV)

   (IV)

wherein X, R, R', a and b have the meanings given in claim 1 and (a+b)=3, with a compound B' having at least two acrylate groups, methacrylate groups, or a combination thereof.

13. The silane of claim 1, wherein said silane has the formula:

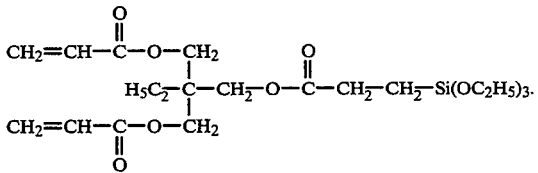

14. The silane of claim 1, wherein said silane has the formula:

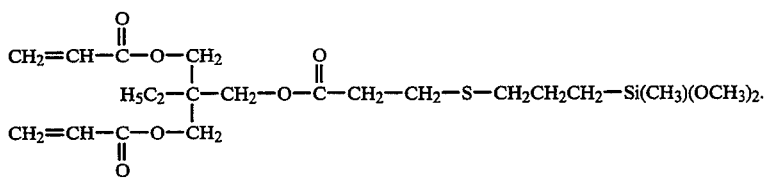

15. The silane of claim 1, wherein said silane has the formula:

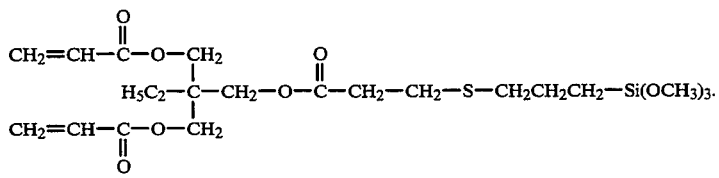

16. The silane of claim 1, wherein said silane has the formula:

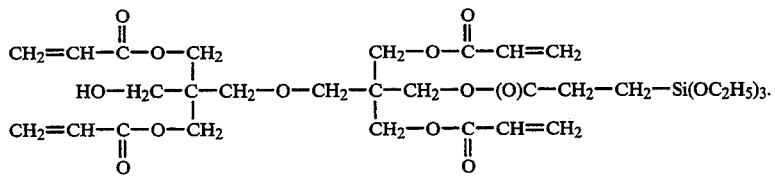

17. The silane of claim 1, wherein said silane has the formula:

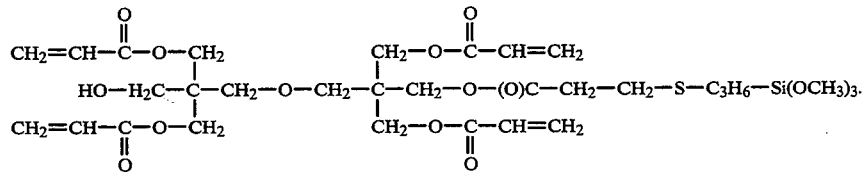

18. The silane of claim 1, wherein said silane has the formula:

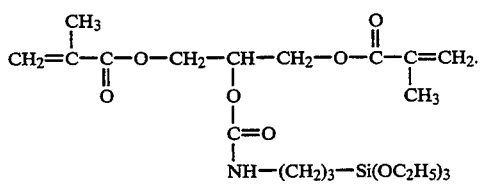

* * * * *